United States Patent
Muenzer et al.

(10) Patent No.: US 11,358,077 B2
(45) Date of Patent: Jun. 14, 2022

(54) BOTTLE-PROCESSING MACHINE AND METHOD FOR CLEANING THE PUMP/NOZZLE PROTECTOR OF THE BOTTLE-PROCESSING MACHINE

(71) Applicant: Krones AG, Neutraubling (DE)

(72) Inventors: Jan Muenzer, Harrislee (DE); Michael Schubert, Flensburg (DE)

(73) Assignee: Krones AG, Neutraubling (DE)

( * ) Notice: Subject to any disclaimer, the term of this patent is extended or adjusted under 35 U.S.C. 154(b) by 15 days.

(21) Appl. No.: 16/099,351

(22) PCT Filed: Nov. 17, 2017

(86) PCT No.: PCT/EP2017/079604
§ 371 (c)(1),
(2) Date: Nov. 6, 2018

(87) PCT Pub. No.: WO2018/177575
PCT Pub. Date: Oct. 4, 2018

(65) Prior Publication Data
US 2020/0047092 A1    Feb. 13, 2020

(30) Foreign Application Priority Data
Mar. 31, 2017   (DE) ............... 10 2017 205 551.0

(51) Int. Cl.
*B01D 33/46* (2006.01)
*A23L 2/46* (2006.01)
(Continued)

(52) U.S. Cl.
CPC .............. *B01D 33/466* (2013.01); *A23L 2/46* (2013.01); *A61L 2/18* (2013.01); *A61L 2/26* (2013.01);
(Continued)

(58) Field of Classification Search
None
See application file for complete search history.

(56) References Cited

U.S. PATENT DOCUMENTS

| | | | | |
|---|---|---|---|---|
| 1,423,342 A | * | 7/1922 | Loew | B08B 3/14 |
| | | | | 134/104.4 |
| 1,678,780 A | * | 7/1928 | Ladd | B08B 9/28 |
| | | | | 134/50 |

(Continued)

FOREIGN PATENT DOCUMENTS

| CN | 2764464 Y | 3/2006 |
|---|---|---|
| CN | 204051185 | 12/2014 |

(Continued)

OTHER PUBLICATIONS

International Search Report and Written Opinion dated Sep. 3, 2018, on application No. PCT/EP2017/079604.

(Continued)

*Primary Examiner* — Robert J Popovics
(74) *Attorney, Agent, or Firm* — Lowenstein Sandler LLP

(57) ABSTRACT

The present disclosure relates to a bottle treatment machine including a pump/nozzle protector in the form of a screen. The screen includes an at least partially perforated surface and the screen is provided for passing a liquid of the bottle treatment machine therethrough. The bottle treatment machine further includes at least one scraper which rests at least partially on the at least partially perforated surface of the screen. The screen and the at least one scraper are arranged to be rotatable relative to one another. The present disclosure further relates to a method for cleaning the screen of the bottle treatment machine.

11 Claims, 8 Drawing Sheets

(51) Int. Cl.

| | | |
|---|---|---|
| *A61L 2/18* | (2006.01) | |
| *A61L 2/26* | (2006.01) | |
| *B01D 33/06* | (2006.01) | |
| *B08B 1/00* | (2006.01) | |
| *B08B 1/02* | (2006.01) | |
| *B08B 1/04* | (2006.01) | |
| *B08B 9/28* | (2006.01) | |
| *B67C 3/00* | (2006.01) | |
| *C02F 1/00* | (2006.01) | |

(52) U.S. Cl.
 CPC .............. *B01D 33/06* (2013.01); *B08B 1/005* (2013.01); *B08B 1/02* (2013.01); *B08B 1/04* (2013.01); *B08B 9/28* (2013.01); *B67C 3/001* (2013.01); *C02F 1/004* (2013.01); *A23V 2002/00* (2013.01); *A61L 2202/15* (2013.01); *A61L 2202/23* (2013.01); *C02F 2303/16* (2013.01)

(56) References Cited

U.S. PATENT DOCUMENTS

| | | | | |
|---|---|---|---|---|
| 1,678,796 A | * | 7/1928 | Williams | B08B 9/28 134/52 |
| 1,923,743 A | * | 8/1933 | Perkins | B08B 9/36 15/59 |
| 1,979,383 A | * | 11/1934 | Gruetter | B08B 3/14 210/403 |
| 2,050,007 A | * | 8/1936 | Forrest | B01D 37/00 210/396 |
| 2,120,455 A | | 6/1938 | Barnebl | |
| 2,167,322 A | * | 7/1939 | Cuno | B01D 29/682 210/392 |
| 2,253,912 A | * | 8/1941 | McKinley | B08B 9/42 134/23 |
| 2,282,187 A | * | 5/1942 | Herold | A23L 3/04 426/407 |
| 2,311,391 A | * | 2/1943 | Herold | B08B 3/14 134/36 |
| 2,363,840 A | * | 11/1944 | Denhard | B01D 33/073 210/396 |
| 2,410,380 A | * | 10/1946 | Jamieson | B08B 3/14 134/104.4 |
| 2,573,169 A | * | 10/1951 | Gerlach | B08B 3/14 134/152 |
| 2,652,841 A | * | 9/1953 | Kurt | A47L 15/245 134/46 |
| 2,710,818 A | * | 6/1955 | Winters | B08B 9/42 134/32 |
| 2,761,799 A | * | 9/1956 | Schroeder | B08B 3/14 100/145 |
| 2,832,474 A | | 4/1958 | Green | |
| 3,113,890 A | * | 12/1963 | Johnson | D21H 25/10 118/249 |
| 3,162,204 A | * | 12/1964 | Babunovic | B08B 9/083 134/104.4 |
| 3,226,749 A | * | 1/1966 | Ziche | B08B 9/20 15/4 |
| 3,292,201 A | * | 12/1966 | Bedard | D21G 3/00 15/256.51 |
| 3,333,700 A | * | 8/1967 | Coleman | B01D 35/28 210/393 |
| 3,520,410 A | * | 7/1970 | Hutto, Jr. | B01D 33/06 210/791 |
| 3,732,877 A | * | 5/1973 | Kloeg | A47L 15/4204 134/111 |
| 3,868,960 A | * | 3/1975 | Cove | B08B 9/30 134/32 |
| 3,869,389 A | * | 3/1975 | Rokitansky | B01D 37/02 210/791 |
| 3,946,750 A | * | 3/1976 | Fischer | B08B 3/14 134/104.4 |
| 4,041,963 A | * | 8/1977 | Babunovic | B08B 9/083 134/147 |
| 4,044,783 A | * | 8/1977 | Babunovic | B08B 3/14 134/104.4 |
| 4,061,152 A | * | 12/1977 | Babunovic | B08B 9/28 134/152 |
| 4,108,774 A | * | 8/1978 | Babunovic | B08B 3/14 210/167.01 |
| 4,147,634 A | * | 4/1979 | Wegener | B01D 33/466 210/396 |
| 4,185,647 A | * | 1/1980 | Babunovic | B08B 9/30 134/60 |
| 4,209,344 A | * | 6/1980 | Simon | B08B 9/22 134/25.4 |
| 4,220,540 A | * | 9/1980 | Hagihara | B01D 29/33 210/415 |
| 4,224,138 A | * | 9/1980 | Kruyer | C10C 3/007 208/391 |
| 4,236,995 A | * | 12/1980 | Kruyer | C10C 3/007 208/391 |
| 4,263,254 A | * | 4/1981 | Huling | A23L 3/04 422/25 |
| 4,265,705 A | * | 5/1981 | Pyykkonen | D21G 3/005 100/174 |
| 4,279,858 A | * | 7/1981 | Huling | A23L 3/04 422/105 |
| 4,331,629 A | * | 5/1982 | Huling | A23L 3/04 422/105 |
| 4,394,867 A | * | 7/1983 | Ciongwa | B08B 3/14 134/104.4 |
| 4,441,406 A | * | 4/1984 | Becker | A23L 3/003 422/25 |
| 4,490,401 A | * | 12/1984 | Becker | A23L 3/003 426/407 |
| 4,498,934 A | * | 2/1985 | Potts | B08B 3/022 134/29 |
| 4,511,461 A | * | 4/1985 | Kruyer | B03B 1/04 209/47 |
| 4,673,496 A | * | 6/1987 | Turner, Jr. | B01D 33/073 210/402 |
| 4,704,958 A | * | 11/1987 | Braymand | A23L 3/04 99/470 |
| 4,740,311 A | * | 4/1988 | Kruyer | B01D 17/12 210/669 |
| 4,744,889 A | * | 5/1988 | Kruyer | B01D 17/0202 209/9 |
| 4,880,539 A | * | 11/1989 | Crawford | B01D 29/6476 209/381 |
| 4,957,630 A | * | 9/1990 | Bratten | B01D 33/39 210/402 |
| 5,032,229 A | * | 7/1991 | Boucher | D21G 3/005 15/256.51 |
| 5,262,069 A | * | 11/1993 | Kato | B01D 33/808 210/791 |
| 5,310,566 A | * | 5/1994 | Baudendistel | A23L 3/003 426/231 |
| 5,417,231 A | * | 5/1995 | Frederiksen | B08B 3/042 134/111 |
| 5,551,334 A | * | 9/1996 | Cody | A23B 4/0056 34/208 |
| 5,558,042 A | * | 9/1996 | Bradley | A01K 63/045 119/226 |
| 5,665,245 A | * | 9/1997 | Kloss | B01D 21/00 210/744 |
| 5,772,958 A | * | 6/1998 | Nielsen | A23L 3/003 134/131 |
| 5,779,901 A | * | 7/1998 | Mosca | B01D 29/48 210/411 |
| 5,815,544 A | | 9/1998 | Lefter | |
| 5,897,788 A | * | 4/1999 | Ketolainen | B01D 33/466 210/784 |
| 6,022,451 A | * | 2/2000 | Macierewicz | D21G 3/005 162/272 |
| 6,142,065 A | * | 11/2000 | Panella | A23L 3/04 99/468 |

(56) References Cited

U.S. PATENT DOCUMENTS

| | | | | |
|---|---|---|---|---|
| 6,177,021 B1* | 1/2001 | Matusch | B04B 11/08 | 210/791 |
| 6,352,021 B1* | 3/2002 | Panella | A23L 3/003 | 99/330 |
| 6,588,327 B2* | 7/2003 | Wakabayashi | A23L 3/003 | 99/367 |
| 6,906,227 B2* | 6/2005 | Neumann | C07C 37/70 | 210/402 |
| 7,037,437 B2* | 5/2006 | Sawhill | A23B 4/26 | 210/784 |
| 7,083,735 B2* | 8/2006 | Laing | B01D 29/114 | 210/791 |
| 7,104,465 B2* | 9/2006 | Persoons | A23L 3/001 | 239/100 |
| 7,464,559 B2* | 12/2008 | Chu | A23L 3/36 | 426/407 |
| 7,600,542 B2* | 10/2009 | Wiedemann | A23L 3/001 | 141/85 |
| 8,281,936 B2* | 10/2012 | Grace | B01D 33/742 | 210/402 |
| 8,640,719 B2* | 2/2014 | Gmeiner | B08B 9/42 | 134/137 |
| 8,694,151 B2* | 4/2014 | Jendrichowski | B65G 47/912 | 700/213 |
| 8,839,596 B2* | 9/2014 | Schiller | B08B 9/083 | 53/376.6 |
| 8,900,373 B2* | 12/2014 | Molitor | B08B 9/34 | 134/22.18 |
| 9,180,498 B2* | 11/2015 | Jendrichowski | B08B 9/423 | |
| 9,199,286 B2* | 12/2015 | Jendrichowski | B08B 9/34 | |
| 9,205,158 B1* | 12/2015 | Jacob | A61L 2/04 | |
| 9,296,026 B2* | 3/2016 | Teruggi | B08B 7/02 | |
| 9,352,366 B2* | 5/2016 | Yamada | B08B 9/083 | |
| 9,511,397 B2* | 12/2016 | Kappel | B67C 3/001 | |
| 9,561,946 B2* | 2/2017 | Schulz | B67C 3/22 | |
| 9,578,894 B2* | 2/2017 | Nielsen | A23L 3/04 | |
| 9,796,004 B2* | 10/2017 | Previero | B08B 9/38 | |
| 9,943,093 B2* | 4/2018 | Adam | A23L 3/003 | |
| 9,957,181 B2 | 5/2018 | Muenzer | | |
| 10,646,801 B2* | 5/2020 | Tameroglu | B01D 29/35 | |
| 11,207,617 B2* | 12/2021 | Arai | B01D 29/6476 | |
| 2003/0070754 A1* | 4/2003 | Francis | B08B 9/083 | 156/709 |
| 2005/0126656 A1* | 6/2005 | Wiedemann | A23L 3/001 | 141/144 |
| 2009/0211606 A1* | 8/2009 | Molitor | B08B 9/20 | 134/18 |
| 2009/0260952 A1* | 10/2009 | Jendrichowski | B65G 21/2072 | 198/442 |
| 2009/0280222 A1* | 11/2009 | Nielsen | A23L 3/02 | 426/232 |
| 2010/0037925 A1* | 2/2010 | Kappel | B67C 3/005 | 134/166 R |
| 2010/0136159 A1* | 6/2010 | Bernhard | B65G 29/00 | 425/534 |
| 2010/0174394 A1* | 7/2010 | Jendrichowski | B65G 47/912 | 700/108 |
| 2010/0186347 A1* | 7/2010 | Munzer | A23L 3/02 | 53/127 |
| 2010/0200020 A1* | 8/2010 | Gmeiner | B08B 9/42 | 134/23 |
| 2010/0212140 A1* | 8/2010 | Jendrichowski | F16M 5/00 | 29/525.06 |
| 2010/0269322 A1* | 10/2010 | Jendrichowski | B23K 37/0443 | 29/428 |
| 2010/0326927 A1 | 12/2010 | Dendle et al. | | |
| 2011/0067730 A1* | 3/2011 | Folz | B08B 9/46 | 134/7 |
| 2011/0100505 A1* | 5/2011 | Jendrichowski | B08B 9/34 | 141/92 |
| 2011/0204004 A1* | 8/2011 | Bremner | C02F 9/00 | 210/805 |
| 2012/0312419 A1* | 12/2012 | Wagner | A23C 3/027 | 141/11 |
| 2014/0110360 A1* | 4/2014 | Braun | B01D 35/02 | 210/805 |
| 2015/0368135 A1* | 12/2015 | Muenzer | B01D 29/50 | 210/149 |
| 2016/0059281 A1* | 3/2016 | Previero | B08B 9/083 | 15/93.1 |
| 2019/0030574 A1* | 1/2019 | Alvarez | B01D 17/0208 | |
| 2020/0047092 A1* | 2/2020 | Muenzer | B08B 9/28 | |
| 2021/0060460 A1* | 3/2021 | Arai | A23L 5/20 | |

FOREIGN PATENT DOCUMENTS

| | | | | |
|---|---|---|---|---|
| CN | 205649921 U | 10/2016 | | |
| CN | 205925162 U | 2/2017 | | |
| DE | 10 22 453 B | 1/1958 | | |
| DE | 11 82 975 B | 12/1964 | | |
| DE | 14 92 581 A1 | 8/1969 | | |
| DE | 39 34 797 A1 | 5/1991 | | |
| DE | 101 57 853 A1 | 6/2003 | | |
| DE | 10 2014 108 798 A1 | 12/2015 | | |
| DE | 102017205551 A1 * | 10/2018 | | C02F 1/004 |
| EP | 2 604 350 A1 | 6/2013 | | |
| EP | 2 959 782 A2 | 12/2015 | | |
| FR | 2 612 080 A1 | 9/1988 | | |
| GB | 2 106 003 A | 4/1983 | | |
| JP | 2014-012256 A | 1/2014 | | |
| WO | 02/30543 A1 | 4/2002 | | |
| WO | WO-2018177575 A1 * | 10/2018 | | B08B 1/005 |

OTHER PUBLICATIONS

German Search Report dated Nov. 7, 2018, on application No. 10 2017 205 551.0.

Chinese Office Action dated May 6, 2020, application No. 201780028844.9.

* cited by examiner

BOTTLE-PROCESSING MACHINE AND METHOD FOR CLEANING THE PUMP/NOZZLE PROTECTOR OF THE BOTTLE-PROCESSING MACHINE

RELATED APPLICATIONS

This Application claims the benefit under 35 U.S.C. § 371 of International Patent Application No. PCT/EP2017/079604, filed Nov. 17, 2017, which claims the benefit of German Application No. 10 2017 205 551.0, filed Mar. 31, 2017, which are incorporated by reference in their entirety.

TECHNICAL FIELD

The present disclosure relates to a bottle treatment machine and to a method of cleaning the pump/nozzle protection of the bottle treatment machine.

BACKGROUND

The necessary process water in a closed circuit may be reused after a treatment step for further process steps in bottle treatment machines. In a bottle treatment machine, the water may contain foreign matter, such as label residues, shards of glass and/or glue residuals, after a treatment step of the bottles. This foreign matter may, in a subsequent treatment cycle, clog the pumps and the nozzles connected thereto for the treatment. In order to prevent this, a pump/nozzle protection in the form of a screening belt discharge or screens which have to be cleaned manually are used.

DE 10 2014 108 798 A1 discloses that screening belts are typically used for separating particles, such as glass shards, sand and/or settling sediments, from the process water of a pasteurization system. These screens may be clogged by suspended sediments, mucilage and substances floating on the water. The mentioned materials deposit, for example, on the screen surfaces where they accumulate. There, these substances increasingly obstruct the screen throughput. Hence, the screens must be checked regularly for obstruction and cleaned. Especially when plug-in screens are used, it may become necessary to pull out and clean these plug-in screens, so that systems with plug-in screens lead to a high workload and/or personnel deployment.

BRIEF DESCRIPTION OF THE DRAWINGS

Embodiments of the present disclosure are illustrated by way of example, and not by way of limitation, in the figures of the accompanying drawings.

DETAILED DESCRIPTION

Figure 1:
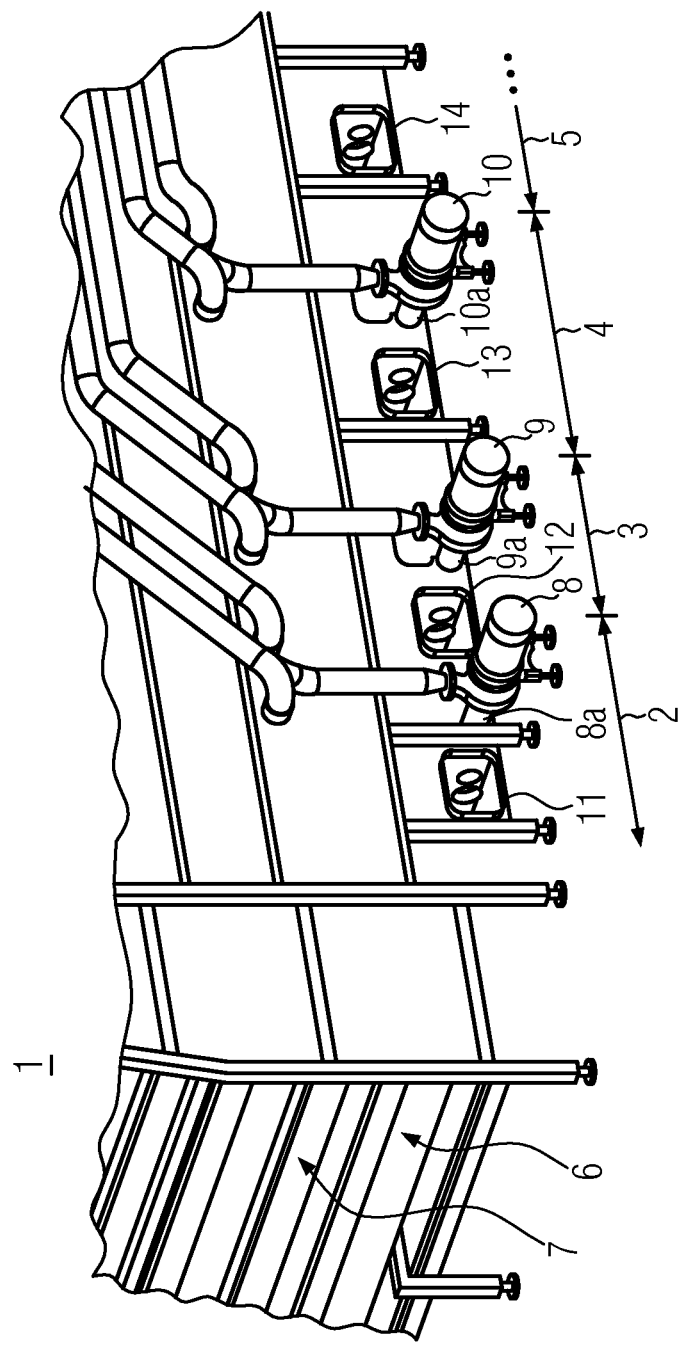
FIG. 1 illustrates a bi-level pasteurizer, according to certain embodiments.

The present disclosure provides a pump/nozzle protection for a bottle treatment machine, which allows process-effective and reliable cleaning of the pump/nozzle protection for operation of the bottle treatment machine.

The present disclosure describes a bottle treatment machine and a method for cleaning a pump/nozzle protection of the bottle treatment machine.

The bottle treatment machine according to the present disclosure, such as a pasteurizer or a bottle cleaning machine, includes a pump/nozzle protection in the form of a screen, where the screen includes an at least partially perforated surface and where the screen is provided for passing a liquid of the bottle treatment machine therethrough. The bottle treatment machine further includes at least one scraper, which rests at least partially on the perforated surface of the screen, the screen and the at least one scraper being arranged such that they are rotatable relative to one another.

In the bottle treatment machine, liquid, such as water, may be applied to the bottles for the purpose of pasteurization or cleaning. Instead of water, a lye (e.g., a cleaning lye of a bottle washing machine), an acid, or some other liquid on the basis of water or on some other basis may be used. Instead of bottles, other containers, such as cans, may be treated. After such treatment steps, the liquid can be collected and guided by a liquid line to the screen. After the treatment steps, the liquid may also include foreign matter, such as contaminations that adhered to the bottles before, label residues and/or glue residuals. This liquid passes through the screen through the at least partially perforated surface of the screen. The at least partially perforated surface of the screen includes a plurality of perforations. By mechanical interaction between the at least partially perforated surface of the screen and the liquid, the foreign matter can be screened out, at least partially, from the liquid.

The cross-section of the perforations may be round, approximately round or hexagonal. Also other cross-sectional shapes are possible. In some embodiments, the perforations are arranged evenly.

The dimensions of the perforations (e.g., the cross-sectional area and/or the diameter) may be configured in accordance with a mean size and/or quantity of the foreign matter to be expected in the liquid. For example, the dimensions of the perforations in a bottle treatment machine may be chosen larger than the dimensions of the perforations in a pasteurizer, since the mean size and/or the quantity of foreign matter to be expected in the liquid of the bottle treatment machine may be larger in comparison with the mean size and/or the quantity of foreign matter to be expected in the liquid of the pasteurizer. Such a mean size and/or quantity of foreign matter to be expected in the liquid can be ascertained by an analysis of a liquid sample and can then be regarded as a given magnitude for the respective bottle treatment machine and the respective bottle treatment process. If the dimension of the perforations of the screen of a bottle treatment machine is comparatively larger, the perforations of the screen may not be clogged by the foreign matter of the liquid within a short period of time and a sufficient screening effect of the screen may be achieved, i.e. a sufficient amount of foreign matter being screened out from the liquid.

During the operation of the bottle treatment machine, foreign matter of the liquid is thus deposited in the perforations of the screen and/or on the material surrounding the perforations.

Hence, the screen should be cleaned at predetermined time intervals by the at least one scraper, which rests, at least partially, on the at least partially perforated surface of the screen, i.e. the deposited foreign matter should be removed (i.e., scraped off by the at least one scraper). When it is discussed in the present disclosure that cleaning of the screen is carried out, i.e. the screen is cleaned, this means especially that the screen is scraped, i.e. subjected to a scraping process, by the at least one scraper. Hence, this can be a cleaning operation or cleaning process in the case of which foreign matter residues may remain on the screen and/or in the perforations of the screen. The time intervals at which the screen should be cleaned may be fixed intervals or selectable intervals. In a screen cleaning process, 80% of the deposited foreign matter can be removed, i.e. scraped off. In some embodiments, more than 95% of the deposited foreign matter can be removed (e.g., scraped off) in a screen cleaning process. Since the at least one scraper removes the foreign matter from the surface, but not from the interior of the perforations, foreign matter residues may remain in the perforations. Since the part of the foreign matter outside the perforations is removed by scraping off by the scraper, the structure of the foreign matter can be shredded, e.g. large-size label residues can be shredded, so that, after the end of the scraping process, when the liquid (with the foreign matter contained therein) passes again through the screen, the foreign matter residues in the perforations, which were still there after the cleaning process, will be flushed out of the perforations. The foreign matter contained in the liquid after the scraping process is so small that it will clog neither the pump nor the nozzles and can thus remain in the process liquid up to the next cleaning phase.

The expression cleaning phase may include a more extensive cleaning of the bottle treatment machine carried out at predetermined time intervals, the bottle treatment machine being then not available for the bottle treatment processes (e.g., since it may have been stopped). During the cleaning phase, the liquid, which is present in the bottle treatment machine and which is provided for treating the bottles and may contain foreign matter from previous treatment processes, may be exchanged (i.e., replaced by a liquid containing no foreign matter).

Between two cleaning phases or also during a cleaning phase, the screen can be cleaned at predetermined time intervals by the at least one scraper, which rests, at least partially, on the at least partially perforated surface of the screen, i.e. the deposited foreign matter can be removed (i.e. scraped off by the at least one scraper). The time intervals for cleaning the screen may be shorter than the time intervals between the cleaning phases. The cleaning of the screen may also be carried out during the operation of the bottle treatment machine, i.e. during treatment processes of the bottles in the bottle treatment machine. The foreign matter which has been scraped off (and thus shredded) can remain in the liquid during two cleaning phases, since the foreign matter which has been scraped off does not impair the throughput of liquid through the pump/nozzle protection in the form of a screen. The throughput of liquid may be used for the operation of the bottle treatment machine.

It follows that the bottle treatment machine according to the present disclosure is able to provide a pump/nozzle protection, which is installed in the bottle treatment machine and which, in the case of clogging through foreign matter (e.g., such as suspended sediments and/or mucilage) can be cleaned by a cleaning device (e.g., with at least one scraper) even while the machine is in operation. The throughput of liquid through the pump/nozzle protection, which is used for operation, can thus be maintained or re-established and for operation of the bottle treatment machine up to the next cleaning phase (e.g., a trouble-free operation of the bottle treatment machine up to the next cleaning phase can be guaranteed).

The screen may be configured as a circular cylinder, and the screen may include a longitudinal axle. The at least partially perforated surface of the screen may correspond to a shell of the circular cylinder, i.e. the circular cylinder is configured as a hollow cylinder. The longitudinal axle may correspond to the mathematical longitudinal axis of the circular cylinder. The shell of the circular cylinder may include an inner circumferential surface and an outer circumferential surface. When liquid passes through the pump/nozzle protection, i.e. the screen, the liquid can penetrate through the perforations of the shell from outside into the (hollow) interior of the screen and the liquid can leave the interior of the screen from inside through the perforations to the outside.

The circular cylinder may be a perpendicular (straight) circular cylinder with a height and a first radius describing the inner circumferential surface, and a second radius describing the outer circumferential surface. The thickness of the at least partially perforated surface is given by the difference between the first and second radii. The volume of the circular cylinder is delimited by the circumferential surface and the two circular areas adjoining the circumferential surface at both ends thereof. The two circular areas may not be perforated but made of a continuous material.

Due to the fact that the screen and the at least one scraper are arranged such that they are rotatable relative to one another and the at least one scraper rests at least partially on the at least partially perforated surface of the screen, the at least one scraper can be moved in contact with and over the at least partially perforated surface of the screen.

The at least one scraper may be configured as at least one scraper pair. The use of a scraper pair allows an optimization of the cleaning of the at least partially perforated surface of the screen.

The at least one scraper pair and may include an internal scraper and an external scraper. "Internal" means here that this scraper, i.e. the internal scraper, is arranged within the volume of the circular cylinder, thus resting at least partially on the inner side of the shell (inner circumferential surface) of the circular cylinder. "External" means here that this scraper, i.e. the external scraper, is arranged outside the volume of the circular cylinder, thus resting at least partially on the outer side of the shell (outer circumferential surface).

The internal scraper and the external scraper may be arranged in opposed relationship with one another. "In opposed relationship with one another" means here that the internal scraper and the external scraper are separated from one another by the shell of the circular cylinder, but rest on the at least partially perforated surface of the screen substantially along a shell line. The structural design may also be such that the internal scraper lies on a first shell line and the external scraper lies on a second shell line, the first and second shell lines being different and spaced apart from each other along the circumferential surface. The distance may be measured along the middle circumferential line of the shell of the circular cylinder. A middle circumference of the circular cylinder results from the halved sum of the circumferences of the inner circumferential surface and of the outer circumferential surface. The distance may be 1 centimeter (cm) or more or less than that.

The at least one scraper may be arranged on an attachment device. The attachment device may allow the at least one scraper to be arranged at a predetermined position and with a predetermined orientation relative to the screen and thus also relative to the bottle treatment machine. In addition, the attachment device may cause the at least one scraper to rest, at least partially, on the at least partially perforated surface of the screen. Furthermore, the attachment device may be configured for allowing the scraper to be arranged such that a scraper blade of the scraper applies a predefined force to the at least partially perforated surface of the screen. In the embodiment, in which the at least one scraper is movably connected to the bottle treatment machine (cf. the second and third embodiments of the bottle treatment machine described hereinafter), the attachment device may be configured such that a rotation of the at least one scraper is possible, the relative positioning and orientation of the at least one scraper with respect to the screen and the bottle treatment machine being, however, known. In some embodiments, the attachment device may be connected to the screen. In some embodiments, the attachment device is controllable by a control device of the bottle treatment machine.

The at least one scraper may include metal and/or plastic material. The at least one scraper may include a respective scraper body and a scraper blade. For example, a part of the scraper, e.g. the scraper body, may consist of metal so as to impart to the scraper a stability for a cleaning process of the screen, and another part of the scraper, e.g. the scraper blade, may consist of plastic material so that, in a cleaning process of the screen, the at least partially perforated surface of the screen will be freed from adherent foreign matter through scraping by the scraper blade, without, however, damaging the at least partially perforated surface by the scraper/scraper blade.

The scraper blade may be arranged parallel to the longitudinal axle of the screen. In some embodiments, the length of the scraper may correspond to the height of the circular cylinder. Due to the fact that the scraper is arranged parallel relative to the longitudinal axle of the screen, a comparatively large area of the at least partially perforated surface of the screen is scraped when the screen and/or the scraper rotate relative to each other (e.g., relative to the scraper and/or the screen). For the parallel orientation of the scraper blade, an edge of the scraper blade may be used by way of example.

The scraper blade may apply a predefined force to the at least partially perforated surface of the screen. This predefined force may be used to scrape foreign matter deposited on the screen off when the scraper rotates relative to the screen. If the predefined force were chosen too weak, deposited foreign matter may not be scraped off the screen. If the force were, however, chosen too strong, a rotation of the screen/the scraper relative to the scraper/the screen would only be possible through an increased expenditure of force, since the scraper blade pressing against the screen would hamper the rotation.

An angle between the scraper blade and a tangential plane of the circular cylinder may lie between 15° and 40°. Making use of this mode of arrangement of the scraper relative to the circular cylindrical surface of the screen, the cleaning of the screen, i.e. the scraping off of foreign matter, can be optimized. Since the scraper blade rests at least partially on the at least partially perforated surface of the screen, a contact line corresponding to a shell line on the circular cylinder may be obtained. Through this shell line, a tangential plane is applied to the circular cylinder and the angle between the scraper blade and the tangential plane is determined. In the case of an internal scraper, the contact line/shell line is to lie on the inner surface of the shell of the circular cylinder. In the case of an external scraper, the contact line/shell line is to lie on the outer surface of the shell of the circular cylinder.

In a first embodiment, the at least one scraper may be fixedly connected to the bottle treatment machine and the screen may be configured such that it is rotatable relative to the at least one scraper for executing a cleaning process. Hence, the scraper resting at least partially on the perforated surface of the screen can be moved over the perforated surface through the rotation of the screen, so as to scrape off, e.g. during a cleaning process of the screen, foreign matter which is deposited at or on the screen and which is included in the liquid passing through the screen. Due to the fact that the scraper is fixedly connected to the bottle treatment machine, movable elements here may not be necessary, so that the structural design of the bottle treatment machine can be simpler in comparison with that of a bottle treatment machine in which also the scraper is configured to be rotatable, and possible additional maintenance work of the movable elements can be dispensed with.

The scraper may be fixedly connected to the bottle treatment machine responsive to the scraper substantially not being able to move relative to the bottle treatment machine. During a cleaning process of the screen and due to the fact that the scraper rests at least partially on the at least partially perforated surface of the screen, the scraping off of the foreign matter from the screen may have the effect that part of the scraper is reversibly deformed.

In a second embodiment, the screen may be fixedly connected to the bottle treatment machine and the at least one scraper may be configured such that it is rotatable relative to the screen for executing a cleaning process. Hence, the scraper resting at least partially on the perforated surface of the screen can be moved over the perforated surface through the rotation of the scraper, so as to scrape off, e.g. during a cleaning process of the screen, foreign matter which is deposited at or on the screen and which is included in the liquid passing through the screen. Due to the fact that the screen is fixedly connected to the bottle treatment machine, movable elements here may not be necessary, so that the structural design of the bottle treatment machine can be simpler in comparison with that of a bottle treatment machine in which also the screen is configured to be rotatable, and possible additional maintenance work of the movable elements can be dispensed with.

In a third embodiment, the screen and the at least one scraper may be configured such that they are rotatable for executing a cleaning process. In comparison with a bottle treatment machine, in which either the scraper or the screen are fixedly connected to the bottle treatment machine, this embodiment allows a larger area of the at least partially perforated surface of the screen to be scraped by the at least one scraper during the cleaning process.

The screen may be arranged on a rotating device. In the embodiment in which the screen is movably connected to the bottle treatment machine (cf. the above described first and third embodiments of the bottle treatment machine), the rotating device may be configured such that a rotation of the screen is possible, the relative positioning and orientation of the screen with respect to the at least one scraper and the bottle treatment machine being, however, known. In some embodiments, the attachment device is controllable by a control device of the bottle treatment machine.

The at least one scraper may include one or more cleaning nozzles, which are configured for applying a cleaning liquid, such as water, e.g. heated water, to the at least one scraper and/or the screen. The cleaning nozzles may be arranged on the scraper such that parts of the scraper can be cleaned by the cleaning liquid during the operation of the bottle treatment machine and/or during a cleaning process of the screen. Alternatively or additionally, the one or more cleaning nozzles may be arranged on the scraper such that, during the operation of the bottle treatment machine and/or during the cleaning process of the screen via the cleaning nozzle, a cleaning liquid is applied to the screen (e.g., to the perforations) in the surroundings of the scraper via the cleaning nozzles. In some embodiments, the one or more cleaning nozzles are controllable by a control device of the bottle treatment machine.

Furthermore, the bottle treatment machine may include a control device configured for controlling a rotation of the screen and/or of the at least one scraper to execute a cleaning process.

In some embodiments, the one or more cleaning nozzles of the at least one scraper and/or the rotating device of the screen and/or the attachment device of the at least one scraper may be controllable by the control device.

A method according to the present disclosure (e.g., a computer-controlled method), is used for cleaning the screen in the bottle treatment machine as described herein.

According to the method for cleaning the pump/nozzle protection, the screen and the at least one scraper are rotated relative to one another. According to a first option, the screen is rotated by actuating the rotating device of the screen. According to a second option, the at least one scraper is rotated by actuating the attachment device of the at least one scraper. According to a third option, the screen is rotated by actuating the rotating device of the screen and the at least one scraper is rotated by actuating the attachment device of the at least one scraper. According to the first, second and third options, the rotation can be executed in a first direction, in a second direction or alternately in the first and second directions. The first direction may here e.g. correspond to a clockwise direction and the second direction may be a direction opposite to the clockwise direction. For finishing the cleaning process, the rotation of the screen is finished according to the first option, the rotation of the scraper is finished according to the second option and the rotation of the screen as well as the rotation of the scraper are finished according to the third option.

FIG. 1 shows exemplarily a bi-level pasteurizer 1 as an example for the bottle treatment machine. In different zones 2, 3, 4, 5 of the pasteurizer, the containers (e.g., bottles, cans) passing through the pasteurizer 1 on the two levels 6, 7 can be treated (e.g., through spraying or sprinkling) with liquid (e.g., water, a lye, or an acid).

The medium which then leaves the upper level 7 and the lower level 6 is collected and drained for reuse. A respective collection device 8, 9, 10 is provided for each zone 2, 3, 4, 5. A drain pipe 8a, 9a belonging to the collection device 8, 9, 10 has arranged therein a screen, which is used for passing the liquid therethrough and provided for mechanically screening out foreign matter from the liquid, as well as scrapers resting at least partially on the at least partially perforated surface of the screen. Each of the zones 2, 3, 4, 5 is additionally provided with an access opening 11, 12, 13, 14 allowing access to the screen and the scrapers.

Figure 2:
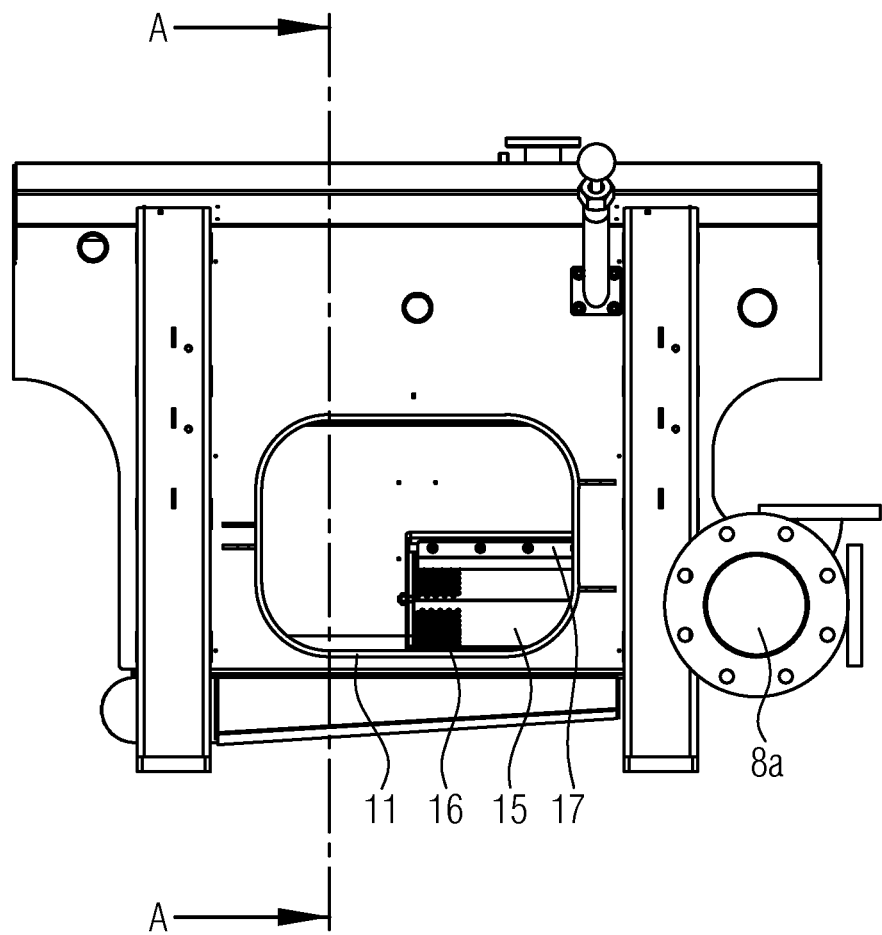
FIG. 2 illustrates a fragmentary side view of a zone of the pasteurizer, seen in the direction in which the drain pipe extends, according to certain embodiments.

FIG. 2 shows a fragmentary side view of a zone 2 of the pasteurizer 1, seen in the direction in which the drain pipe 8a extends. In the access opening 11, the screen 15 with the perforated surface 16 of the screen 15 (illustratively, the perforation is only shown on part of the surface) and an external scraper 17 can be seen. The screen 15 is configured as a circular cylinder and the perforated surface 16 of the screen 15 corresponds to the circumferential surface of the circular cylinder.

Figure 3:
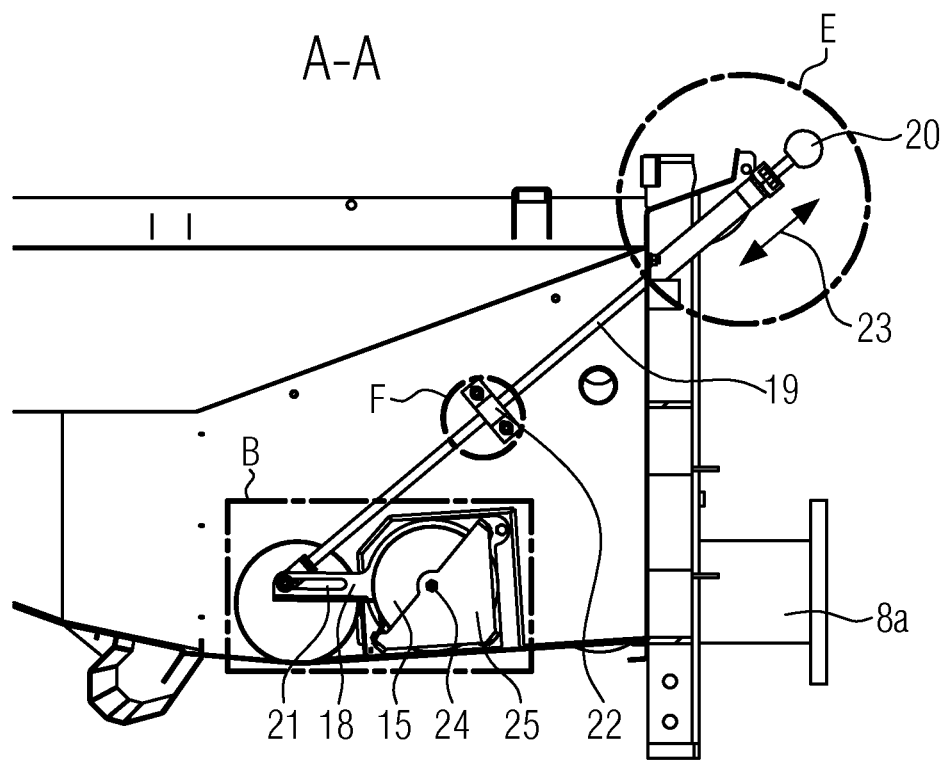
FIG. 3 illustrates a sectional view along line A-A of FIG. 2, according to certain embodiments.

FIG. 3 shows a sectional view along line A-A of FIG. 2. The screen 15 is arranged on a rotating device 18 by which the screen 15 can be rotated relative to the scraper/scrapers about a longitudinal axle 24 of the screen 15. The longitudinal axle 24 corresponds here to the mathematical longitudinal axis of the circular cylinder. The screen 15 may be arranged in the rotating device 18 (e.g., via bearings) in which a rotary shaft of the screen can be supported. The rotating device 18 includes a linkage 19 that extends to an actuating device 20. In addition, the linkage 19 is movably supported in an elongated hole 21 of the rotating device 18. Furthermore, the linkage 19 is secured to the pasteurizer 1 by a clamp 22, the linkage 19 being adapted to move through the clamp 22. By moving the linkage 19 out and in via the actuating device 20 along the direction 23 of an imaginary extension of the linkage, the screen 15 can be rotated about the longitudinal axle 24 via the rotating device 18.

FIG. 3 additionally shows an attachment device 25 having the scrapers 17 arranged thereon. The attachment device can allow the scrapers 17 to be arranged at a predetermined position and with a predetermined orientation relative to the screen 15 and thus also relative to the pasteurizer 1. In addition, it can be guaranteed by the attachment device 25 that the scrapers 17 rest, at least partially, on the perforated surface 16 of the screen 15.

Figure 4:
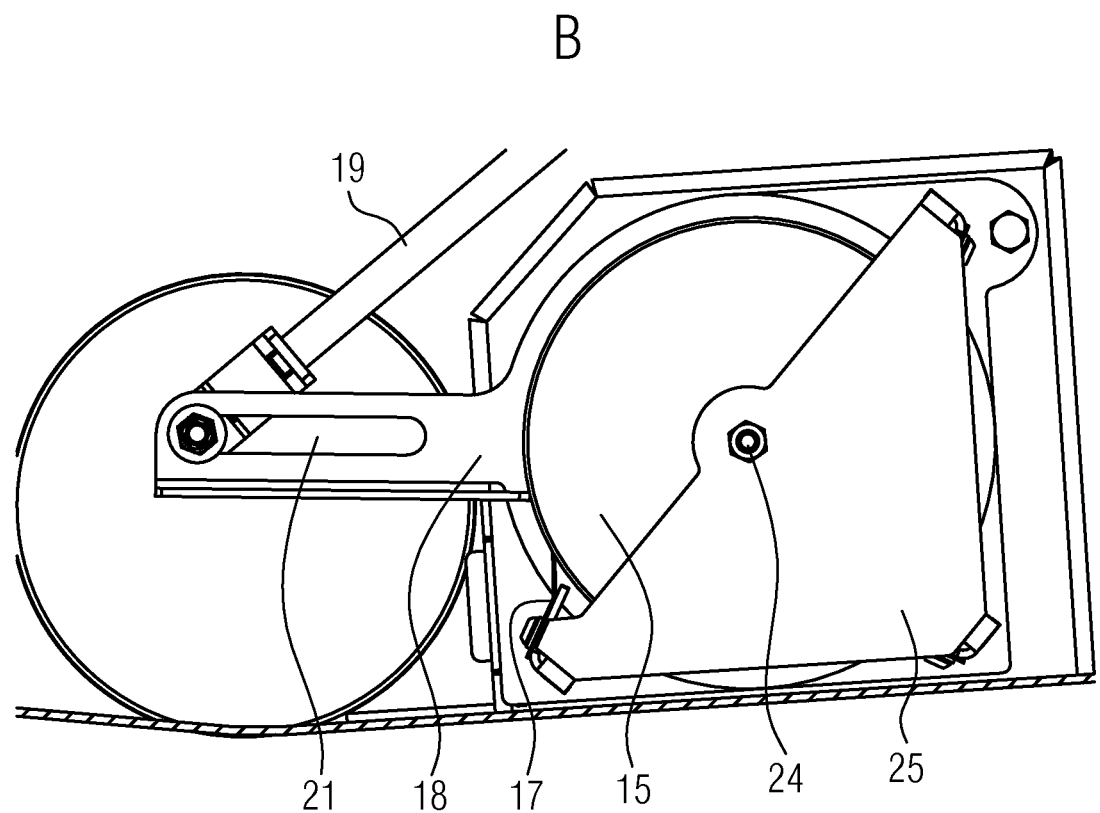
FIG. 4 illustrates an enlarged detail B of FIG. 3, according to certain embodiments.

FIG. 4 shows an enlarged detail B of FIG. 3, in which, among other components, the rotating device 18 of the screen 15 and the attachment device 25 of the scrapers 17 are illustrated.

Figure 5:
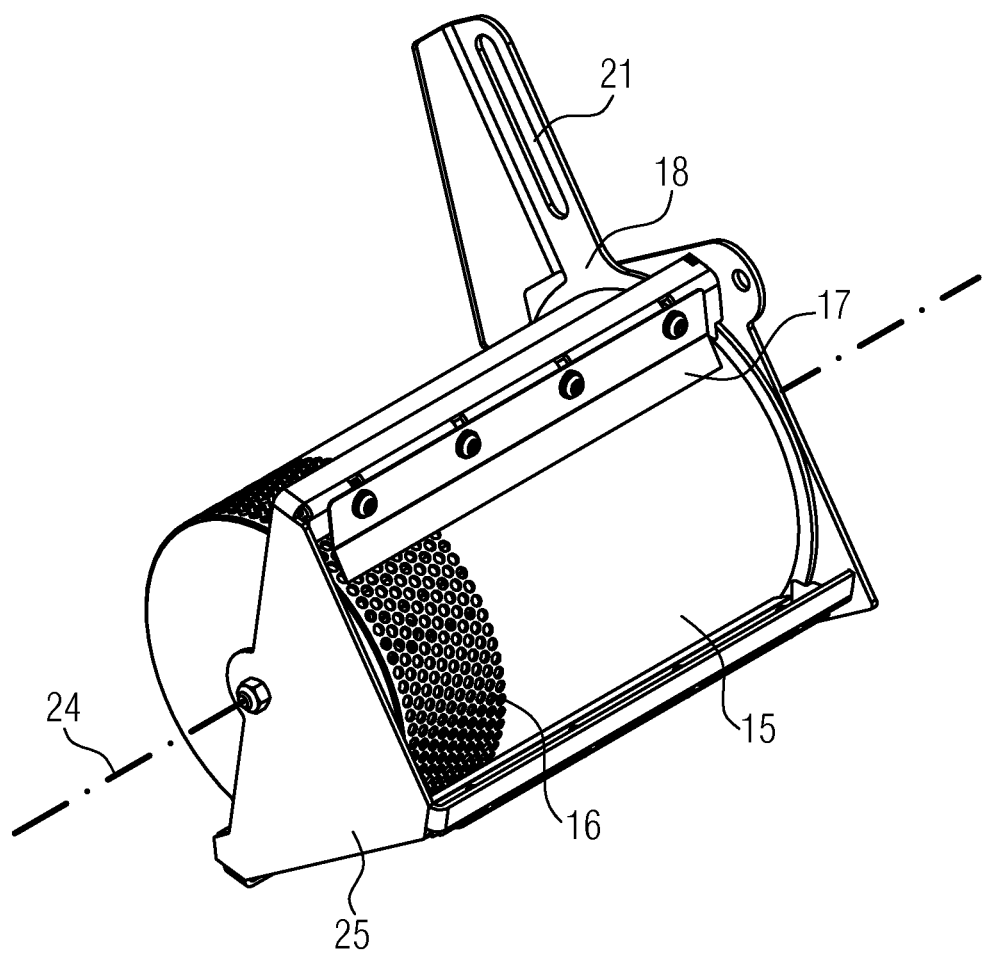
FIG. 5 illustrates a perspective view of the screen together with the screen moving device and the attachment device of the scrapers, according to certain embodiments.

FIG. 5 shows a perspective view of the circular cylindrical screen 15 with the partially perforated surface 16, together with the rotating device 18 of the screen 15, which is configured for rotating the screen 15 about its longitudinal axle 24, and of the attachment device 25 of the scrapers 17, only one scraper 17 being visible in the present representation. The perforations on the circumferential surface of the screen 15 are, illustratively, only shown in a limited area.

Figure 6:
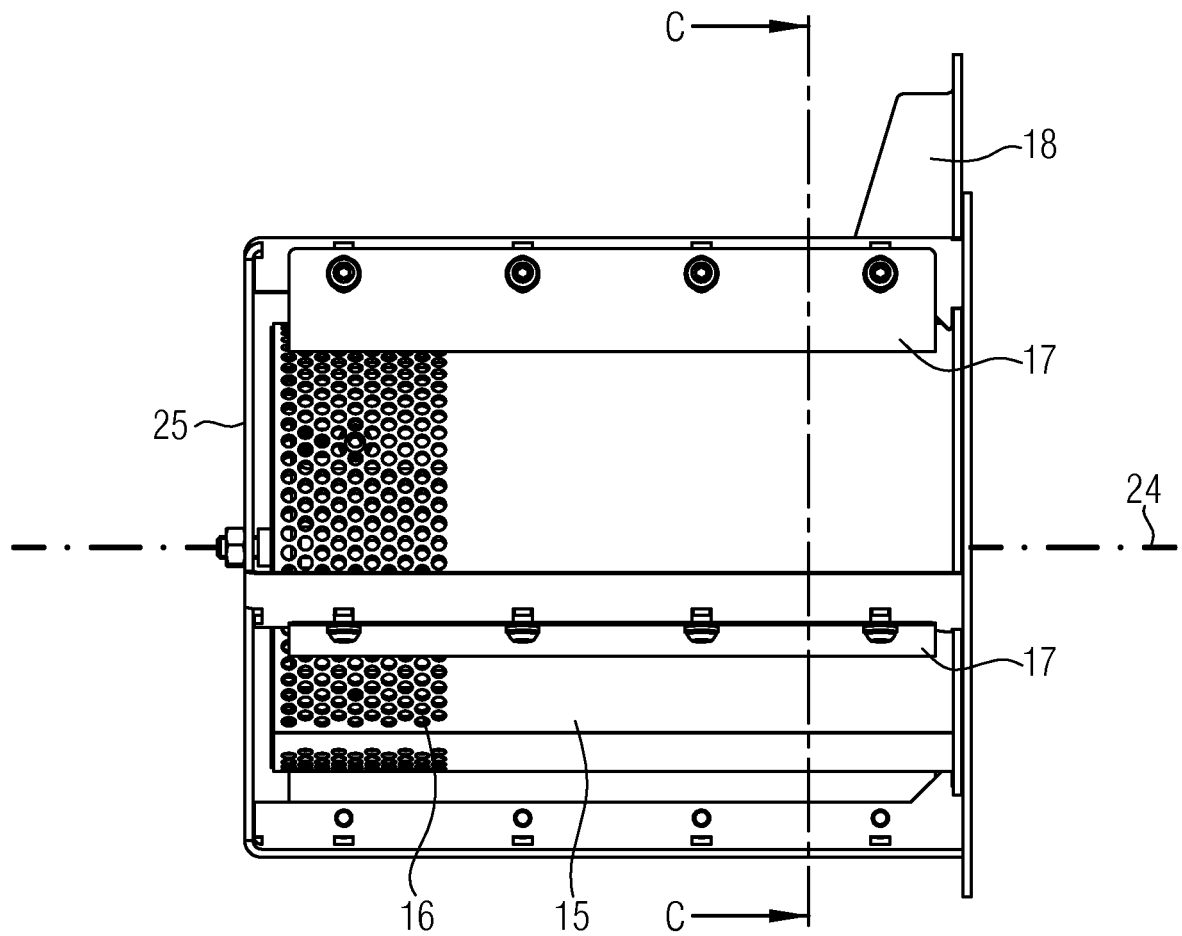
FIG. 6 illustrates a view of the representation according to FIG. 5, seen in a direction perpendicular to the longitudinal axle of the screen, according to certain embodiments.

FIG. 6 shows a view of the representation according to FIG. 5, seen in a direction perpendicular to the longitudinal axle 24 of the screen 15. Two external scrapers 17 are visible. As can also be seen from FIG. 6, "external" means that these two scrapers 17 are arranged outside the volume of the circular cylinder, and rest thus on the outer face of the circumferential surface.

Figure 7:
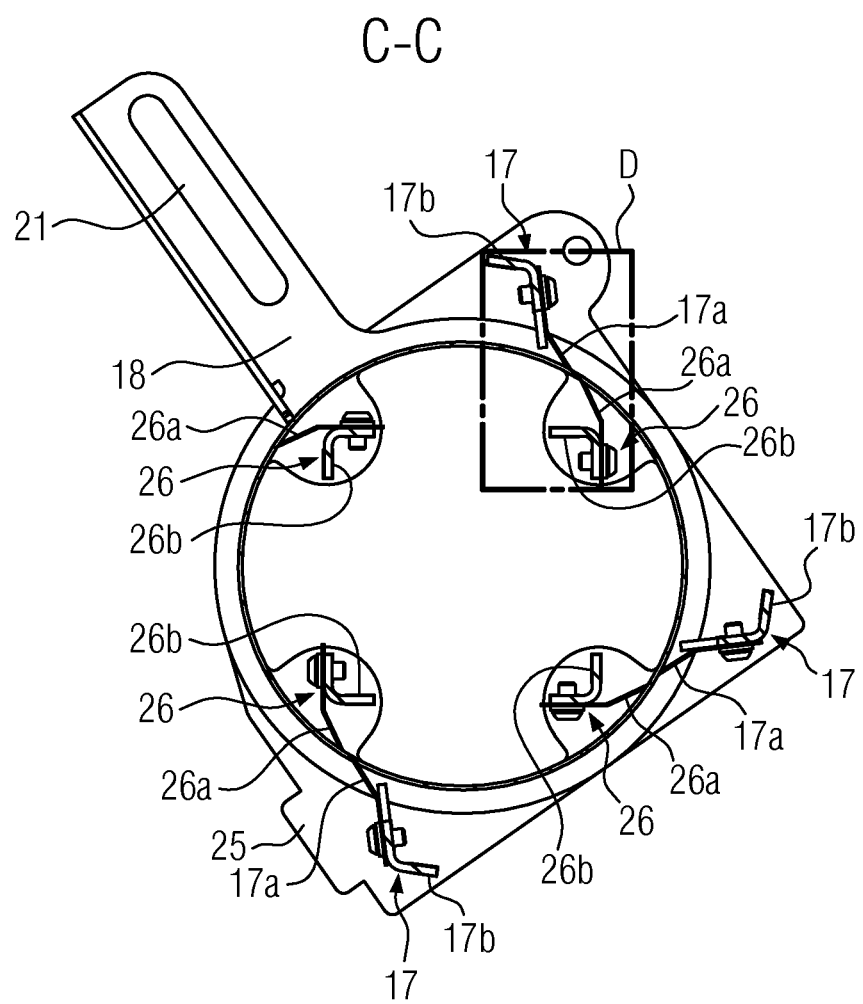
FIG. 7 illustrates the cross-section of FIG. 6 along line C-C, according to certain embodiments.

FIG. 7 shows a cross-section of FIG. 6 along line C-C, in which three external scrapers 17 and four internal scrapers 26 are now shown. "Internal" means here that the four internal scrapers 26 are arranged within the volume of the circular cylinder, and rest thus on the inner shell surface of the circular cylinder. The scrapers 17, 26 each include a scraper body 17b, 26b and a scraper blade 17a, 26a. The scraper body 17b, 26b can impart to a scraper 17, 26 a stability required for a cleaning process of the screen 15; the scraper body 17b, 26b may consist e.g. of metal. The scraper blade 17a, 26a rests at least partially on the at least partially perforated surface 16 of the screen. The scraper blade 17a, 26a may consist e.g. of plastic material so that, in a cleaning process of the screen, the at least partially perforated surface of the screen will be freed from adherent foreign matter through scraping, without, however, damaging the at least partially perforated surface by the scraper/scraper blade.

Figure 8:
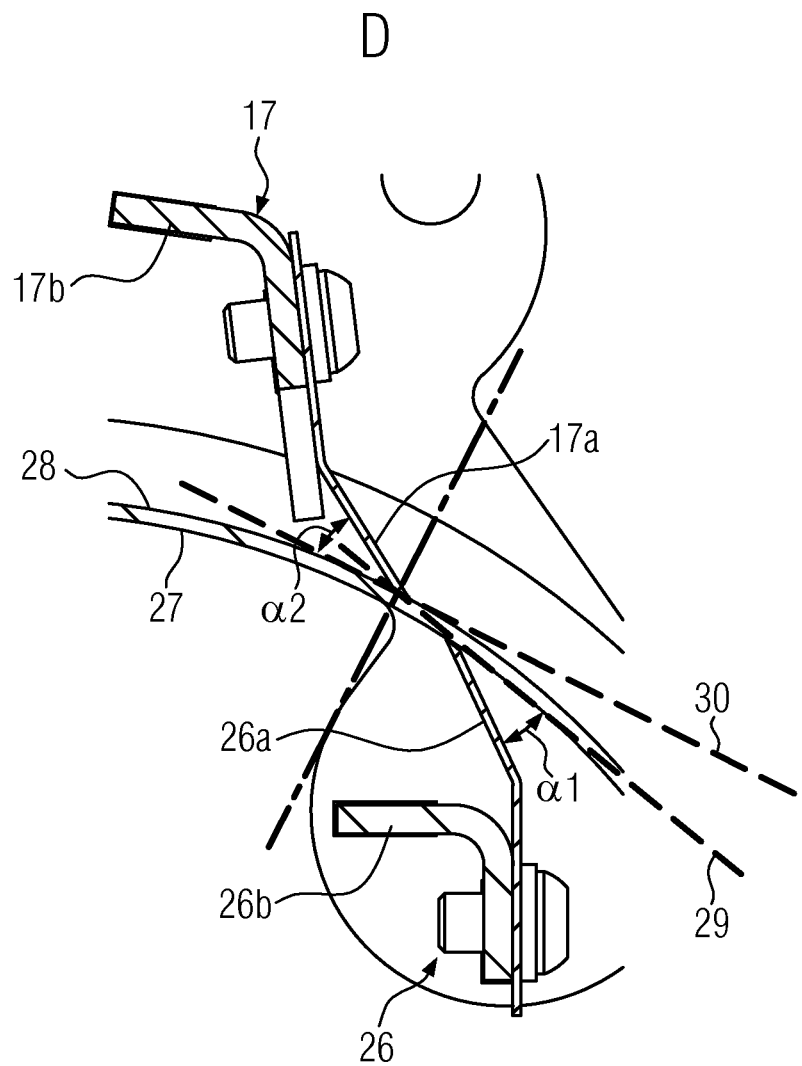
FIG. 8 illustrates the enlarged detail D of FIG. 7, according to certain embodiments.

FIG. 8 shows an enlarged detail D of FIG. 7, in which one of the external scrapers 17 and one of the internal scrapers 26 can be seen, said scrapers abutting on the outer shell surface 28 of the screen 15 and on the inner shell surface 27 of the screen 15, respectively, in substantially opposed relationship with one another.

For the external scraper 17 as well as for the internal scraper 26, the respective angle α1, α2 between the scraper blade 17a, 26a and the tangential plane 30, 29 to the outer shell surface 28 and the inner shell surface 27, respectively, in the contact line of the scraper blade 17a, 26a on the outer 28/inner shell surface 27 is approximately 30°. In FIG. 8, each of the tangential planes 29, 30 is represented by a tangent line. This mode of arrangement of the scrapers relative to the circular cylindrical surface 16, 27, 28 of the screen 15 allows the cleaning of the screen 15, i.e. the scraping off of foreign matter, to be optimized.

The internal scraper 26 and the external scraper 17 are arranged in opposed relationship with one another. The internal scraper 26 and the external scraper 17 are separated by the shell of the circular cylinder. The shell of the circular cylinder is delimited by the outer shell surface 28 and the inner shell surface 27. The internal scraper 26 lies on a first shell line and the external scraper 17 lies on a second shell line, the first and second shell lines being different and spaced apart from one another. The distance may be measured along the middle circumferential line of the shell of the circular cylinder. A middle circumference of the circular cylinder results from the halved sum of the circumferences of the inner circumferential surface and of the outer circumferential surface.

From the representation according to FIG. 8 it can be seen that, when the scrapers 17, 26 rotate relative to the screen 15, when the screen 15 rotates relative to the scrapers 17, 26, or when both the screen 15 and the scrapers 17, 26 rotate, foreign matter, which is scraped off by the external scraper 17 and which, in the course of this process, may perhaps be pressed inwards fully or partly through the perforations, can be scraped off by the internal scraper 26. Foreign matter, which is scraped off by the internal scraper 26 and which, in the course of this process, may perhaps be pressed outwards fully or partly through the perforations, can be scraped off by the external scraper 17 in a corresponding manner.

It is to be understood that the above description is intended to be illustrative, and not restrictive. Many other embodiments will be apparent upon reading and understanding the above description. Although embodiments of the present disclosure have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. In a bottle treatment machine including a housing for receiving bottles to be treated and a liquid circulation circuit including a pump and a nozzle through which liquid to pasteurize and/or clean the bottles can be discharged, the bottle treatment machine further comprising:
   an attachment device;
   a pump/nozzle protection in form of a screen, wherein the screen is coupled to the attachment device, wherein the screen comprises an at least partially perforated surface, wherein the screen is a circular cylinder and the screen comprises a longitudinal axle, wherein the at least partially perforated surface of the screen corresponds to a shell of the circular cylinder, and wherein the screen is provided for passing the liquid of the bottle treatment machine therethrough; and
   a scraper pair that is coupled to the attachment device and that comprises an internal scraper and an external scraper, the internal scraper being arranged within a volume of the circular cylinder, the internal scraper resting at least partially on an inner side of the shell of the circular cylinder, the external scraper being arranged outside the volume of the circular cylinder, the external scraper resting at least partially on an outer side of the shell of the circular cylinder, the internal scraper and the external scraper being arranged in opposed relationship with one another and being separated from one another by the shell of the circular cylinder, the internal scraper lying on a first shell line and the external scraper lying on a second shell line, the first shell line and the second shell line being different and being spaced apart from each other along the shell, and the screen and the scraper pair being arranged to be rotatable relative to one another for executing a cleaning process.

2. The bottle treatment machine of claim 1, wherein:
   the scraper pair comprises at least one of a metal material or a plastic material;
   each scraper of the scraper pair comprises a scraper body and a scraper blade;
   the scraper blade of each scraper of the scraper pair is arranged parallel to the longitudinal axle of the screen and applies a predefined force to the at least partially perforated surface of the screen; and
   an angle between the scraper blade and a tangential plane of the circular cylinder is between 15° and 40°.

3. The bottle treatment machine of claim 1, wherein the scraper pair is not movable relative to the housing of the bottle treatment machine and wherein the screen is rotatable relative to the scraper pair.

4. The bottle treatment machine of claim 1, wherein the screen is not movable relative to the housing of the bottle treatment machine and wherein the scraper pair is rotatable relative to the screen for executing a cleaning process.

5. The bottle treatment machine of claim 1, wherein the screen is arranged on a rotating device.

6. A method for cleaning a pump/nozzle protection of a bottle treatment machine to apply a liquid to bottles to pasteurize or clean the bottles, the bottle treatment machine comprising:
   an attachment device;
   the pump/nozzle protection in form of a screen, wherein the screen is coupled to the attachment device, wherein the screen comprises an at least partially perforated surface, wherein the screen is a circular cylinder and the screen comprises a longitudinal axle, wherein the at least partially perforated surface of the screen corresponds to a shell of the circular cylinder, and wherein the screen is provided for passing the liquid of the bottle treatment machine therethrough; and
   a scraper pair that is coupled to the attachment device and that comprises an internal scraper and an external scraper, the internal scraper being arranged within a volume of the circular cylinder, the internal scraper resting at least partially on an inner side of the shell of the circular cylinder, the external scraper being arranged outside the volume of the circular cylinder, the external scraper resting at least partially on an outer side of the shell of the circular cylinder, the internal scraper and the external scraper being arranged in opposed relationship with one another and being separated from one another by the shell of the circular cylinder, the internal scraper lying on a first shell line and the external scraper lying on a second shell line, the first shell line and the second shell line being different and being spaced apart from each other along the shell, and the screen and the scraper pair being arranged to be rotatable relative to one another, wherein the method comprises:

passing the liquid of the bottle treatment machine through the screen; and rotating one or more of the screen or the scraper pair of the bottle treatment machine for the cleaning of the screen.

7. The method of claim 6, wherein:

the scraper pair comprises at least one of a metal material or plastic material;

each scraper of the scraper pair comprises a scraper body and a scraper blade;

the scraper blade of each scraper of the scraper pair is arranged parallel to the longitudinal axle of the screen and applies a predefined force to the at least partially perforated surface of the screen; and an angle between the scraper blade and a tangential plane of the circular cylinder is between 15° and 40°.

8. The method of claim 6, wherein the rotating of the one or more of the screen or the scraper pair comprises:

rotating the screen relative to the scraper pair for the cleaning of the screen, wherein the scraper pair is not movable relative to the bottle treatment machine.

9. The method of claim 6, wherein the rotating of the one or more of the screen or the scraper pair comprises:

rotating the scraper pair relative to the screen for the cleaning of the screen, wherein the screen is not movable relative to the bottle treatment machine.

10. The method of claim 6, wherein the rotating of the one or more of the screen or the scraper pair comprises:

rotating the screen and the scraper pair for the cleaning of the screen.

11. The method of claim 6, wherein the screen is arranged on a rotating device.

* * * * *